United States Patent

Haan et al.

[11] Patent Number: 6,096,007
[45] Date of Patent: Aug. 1, 2000

[54] PRESSURE CONTAINER FOR APPLYING PRESSURE TO A FLEXIBLE BAG RECEIVED IN IT AND FILLED WITH A MEDICAL FLUID

[75] Inventors: Harald Haan; Pavel Novak, both of Schaffhausen, Switzerland; Stefan Singer, Gottmadingen, Germany; Roland Hübscher, Schlatt, Switzerland; Andreas Bayer, Singen, Germany

[73] Assignee: Storz Endoskop GmbH, Switzerland

[21] Appl. No.: 09/283,482

[22] Filed: Apr. 1, 1999

Related U.S. Application Data

[63] Continuation of application No. PCT/EP98/04814, Jul. 31, 1998.

[51] Int. Cl.$^7$ .................................................. A61M 37/00
[52] U.S. Cl. .......................... 604/147; 604/147; 604/113; 604/258; 222/95
[58] Field of Search .................... 128/DIG. 12; 604/141, 604/145, 147, 113, 258; 222/92, 95

[56] References Cited

U.S. PATENT DOCUMENTS 3,507,278   4/1970   Werding .
3,756,459   9/1973   Bannister .
3,895,741   7/1975   Nugent .
4,673,392   6/1987   Keime .
4,857,055   8/1989   Wang .
5,053,011   10/1991   Strobel et al. .
5,399,166   3/1995   Laing .

*Primary Examiner*—Mark Bockelman
*Attorney, Agent, or Firm*—St. Onge Steward Johnston & Reens LLC

[57] ABSTRACT

A pressure container for applying pressure to a flexible bag received in it and filled with a medical fluid, in order to deliver the fluid from the flexible bag, has a housing that has an opening for introduction of the bag. Also provided are a cover for covering the opening, an aperture for leading a fluid discharge line of the bag out of the pressure container, and a closure for sealed joining of the cover and housing. In the interest of simpler design and easier handling, it is proposed that the housing be configured as an upright hollow-cylindrical body, closed at the bottom and open at the top, the cross section of which has a flattened oval shape and corresponds roughly to the cross-sectional contour of a bag; and that the two opposing large-area upright sidewalls each have, in mirror-image fashion, the shape of a segment of a cylindrical shell whose lateral ends are joined by joining segments.

30 Claims, 8 Drawing Sheets

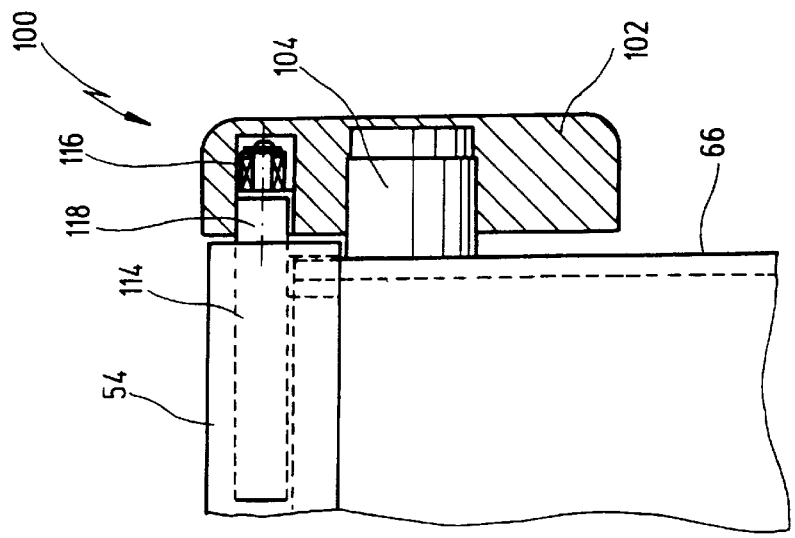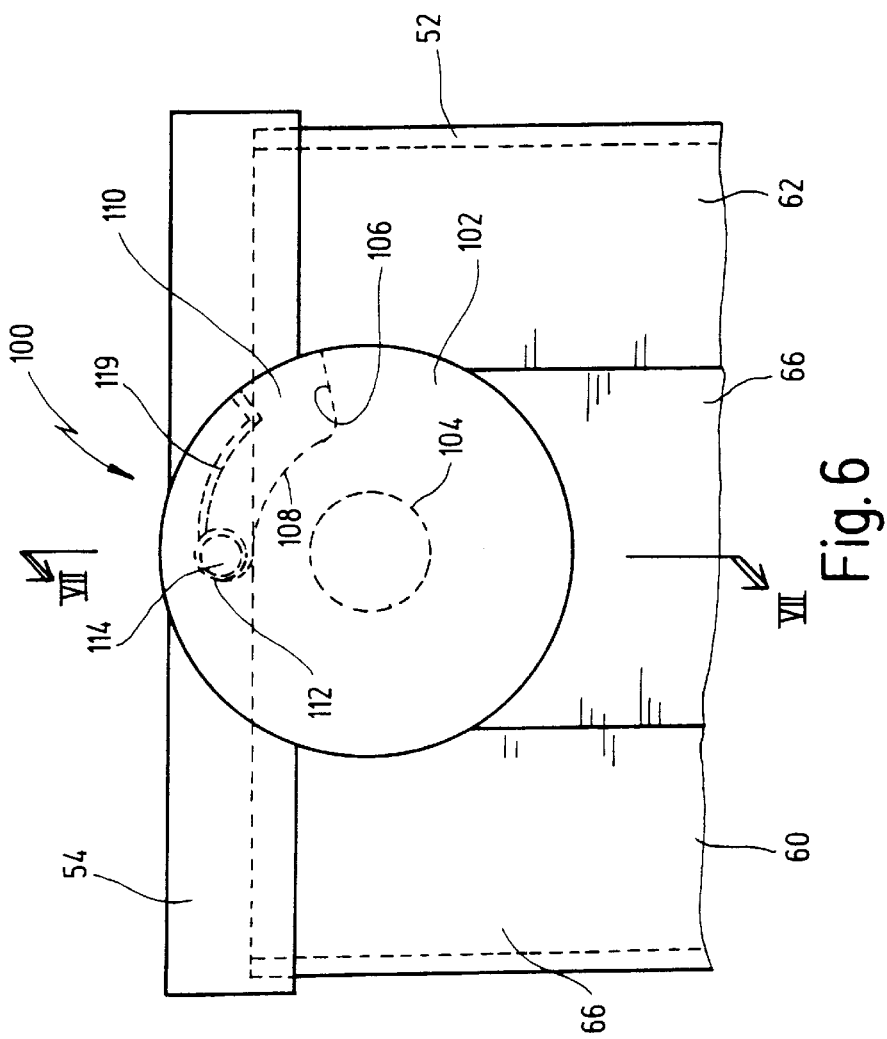

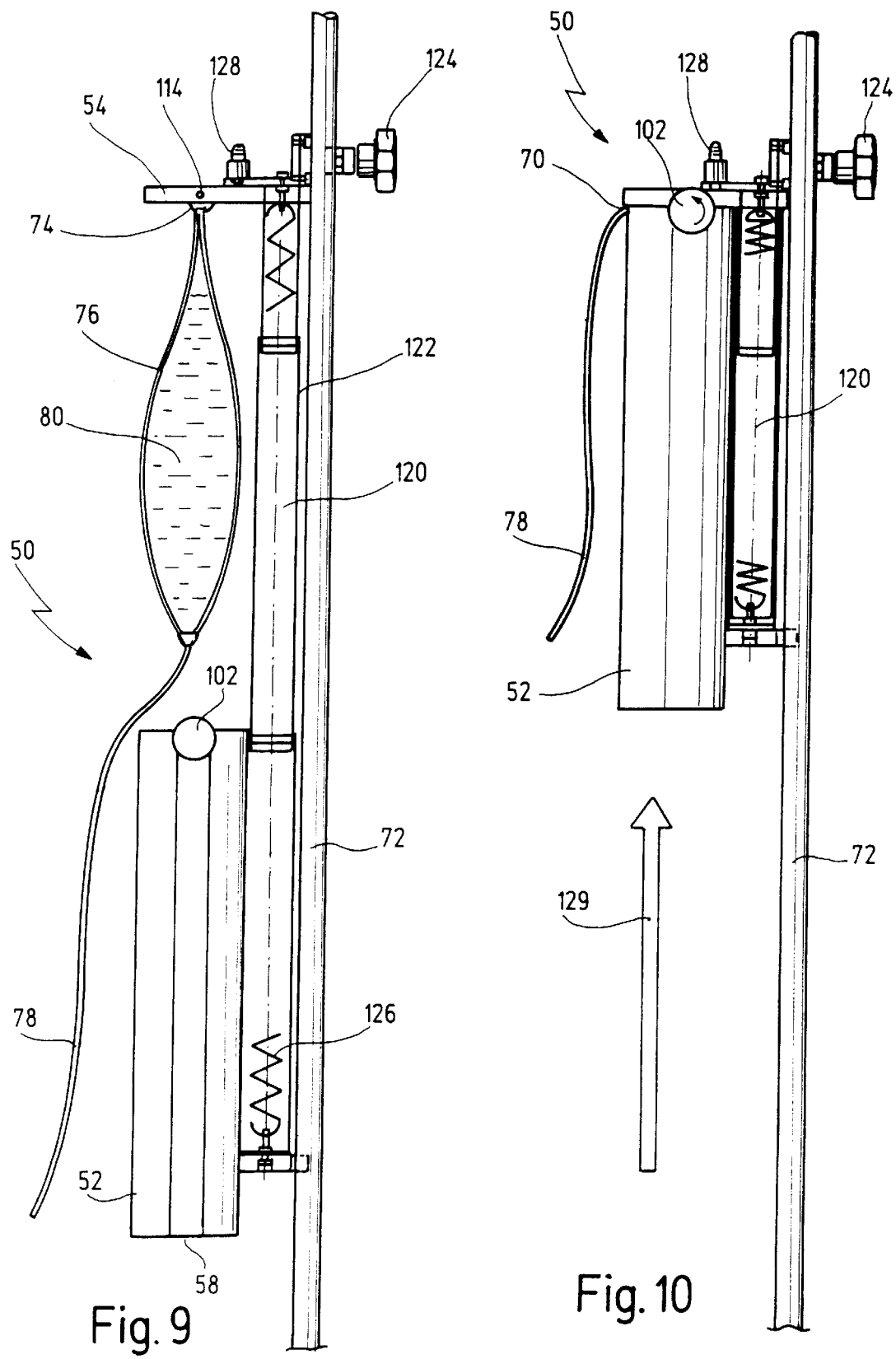

PRESSURE CONTAINER FOR APPLYING PRESSURE TO A FLEXIBLE BAG RECEIVED IN IT AND FILLED WITH A MEDICAL FLUID

This application is a continuation of pending international application PCT/EP98/04814, filed Jul. 31, 1998, which designated the United States.

BACKGROUND OF THE INVENTION

1. Field of the Invention

The invention concerns a pressure container for applying pressure to a flexible bag received in it and filled with a medical fluid, in order to deliver fluid from the flexible bag, having a housing that has an opening for introduction of the bag, having a cover for covering the opening, having an aperture for leading a fluid discharge line of the bag out of the pressure container, and having a closure for sealed joining of the cover and housing.

2. Related Prior Art

A pressure container of this kind is known from DE 41 37 748 A1.

In endoscopic investigations or endoscopic operations, it is often necessary to deliver a medical fluid for irrigating purposes. The pressure container cited initially is used for this purpose. The bag with the medical fluid received therein is introduced, together with its fluid discharge line mounted thereon, into the housing via the opening. The fluid discharge line, usually in the form of a thin tube, must then be either connected to a line leading out of the housing, or threaded through a corresponding opening, which is cumbersome and requires a great deal of attention. The housing is then sealingly closed with the cover via a closure. In the case of DE 41 37 748 A1 mentioned initially, the cover closes off the housing in the manner of a wine barrel, i.e. it is placed against the opening from the inside and locked with an externally rotatable locking element. The housing itself is configured as a rectangular cuboid. For large quantities of fluid (bags with capacities of up to 5 liters are in use), the housing must then be of a corresponding size and must not only withstand the usual pressures during handling, i.e. approximately 1–1.5 bar, but because of certification regulations must resist a test pressure of approx. 4.5 bar.

Handling with the pressure container cited initially is extraordinarily cumbersome; and because of the cuboidal geometry, joined or welded seams—which are correspondingly complex to produce—are provided along the cuboid edges. In the case of large pressure containers in particular, the apparatus is very bulky and extremely heavy.

Further containers of this kind, which in some cases also serve for the aspiration of fluids, are known from DE 25 36 746 C2, DE 28 55 270 A1, DE 35 35 180 A1, EP 0 040 427 A1, and U.S. Pat. No. 5,002,534.

It is therefore the object of the present invention to develop further a pressure container of the kind cited initially in such a way that it is of simple construction and simple to handle, and easily withstands pressure conditions, especially including test pressure conditions.

SUMMARY OF THE INVENTION

According to the present invention, the object is achieved in that the housing is configured as an upright hollow-cylindrical body, closed at the bottom and open at the top, the cross section of which has a flattened oval shape and corresponds roughly to the cross-sectional contour of a bag; and that the two opposing large-area upright sidewalls each have, in mirror-image fashion, the shape of a segment of a cylindrical shell whose lateral ends are joined by joining segments.

As a result of the selection of an upright hollow-cylindrical body open at the top and closed at the bottom, handling is simplified by the fact that the bag can be inserted from above through the opening into the upright hollow cylinder. The fact that its cross section has a flattened oval shape and roughly corresponds to the cross-sectional contour of the bag results in a pressure container whose shape and size correspond approximately to the bag to be received therein, so there is no need to create large and bulky equipment. A bag filled with fluid fits upright in the housing, so that no part of the bag is squeezed or pinched. Because of the choice of the cylindrical shell geometry, the sidewalls easily withstand even a high test pressure of 4.5 bar with a relatively thin wall thickness, with no risk of deformations or bulges.

It is thereby possible to create light, slender, easily handled pressure containers approximately adapted to the shape of the bag. Because of their light weight, the pressure containers can also be mounted, for example, on stands which are used in the medical field for the delivery of fluids. Once the bag has been simply inserted through the oval upper opening and the fluid discharge line has then been supplied, the container needs only to be closed with the cover and joined tightly using the closure. This action can also be easily and reliably performed even by untrained persons. By application of pressure the fluid can then be discharged from the bag in controlled fashion, i.e. in the desired volume per unit time.

In a further embodiment of the invention, the cover is configured as a cover which covers the oval upper opening and overlaps the upper edge.

The advantage of this feature is that this geometry allows simple and reliable placement of the cover on the housing after the bag has been introduced, so that even technically untrained persons can bring the cover into the appropriate closed position and can then create the sealed attachment using the closure.

In a further embodiment of the invention, there is provided in at least one sidewall a viewing window whose pane also has the shape of a cylindrical shell segment, and the pane is placed against the viewing window from the inner side of the housing.

This feature has the advantage that because of the geometry selected, it is possible to use simple and lightweight materials for the viewing window as well, since high pressures can be withstood merely because of the cylindrical shell segment geometry. Because the window is placed against the inner side, it is even further pressed sealingly against the opening by the operating pressure. It is thus also possible to provide large-area windows through which the respective fill level of the bag can be checked visually.

In a further embodiment of the invention, at least one circumferentially or axially extending strip of the material of the sidewall is left behind in the viewing window.

This feature has the advantage, in particular with very large pressure containers having large windows, that on the one hand the strip of material allows the wall in which the window is provided to remain stable, and on the other hand an additional support point is provided for the window placed against the inner side, so that, for example, window materials made of transparent plastic can be utilized.

In a further embodiment of the invention, the closure has at least one turning knob, arranged on the outer side of the housing, on whose inner side is cut out a gated guide into which a gate peg projecting radially from the cover can be introduced; and by rotation of the turning knob, the gate sealingly prevents removal of the cover from the housing.

This feature has the considerable advantage that the closure is closed using simple features that can be carried out in dependable fashion. The cover be placed onto the housing only if the turning knob is in the correct position, specifically if the peg can in fact enter the gated guide. A simple turning operation closes the closure, so that a perfectly sealing and securely closing join between cover and housing is created. This too can be performed by persons with little technical training.

In a further embodiment of the invention, the gate peg has a cylindrical shoulder segment, projecting radially from the cover, adjoining which is an end equipped with a roller, the gated guide being configured such that in a first rotational segment of the roller it runs over a ramp, and only in the end position does an end segment with a stop come to rest against the shoulder segment.

This feature has the considerable advantage, in terms of the service life of the apparatus, that upon rotation of the turning knob, the result of rotatably mounted roller is that the gate peg runs with little friction or resistance in the first rotational segment, and only in the end position does the cover, with its cylindrical shoulder segment, come into contact with the closure under the closing and operating pressure. This not only facilitates handling for opening and closing, but also appreciably increases the service life of the closure.

In a further embodiment of the invention, the gated guide is undercut in the region of the stop.

The advantage of this feature is that because of the undercut, the operator palpably perceives that this region has been reached. Inadvertent or deliberate opening of the closure during pressurized operation is not possible, since that would require first moving the gate peg out of the undercut, which is not possible with manual force. This feature thus contributes substantially to safety during pressurized operation.

In a further embodiment of the invention, a circumferential V-seal is provided between the cover and the upper edge of the body.

The advantage of this feature is that it creates a kind of self-sealing mechanism, since as the applied pressure rises, sealing between the periphery of the housing and the cover is increased due to the V-shaped geometry.

In a further embodiment of the invention, two closures, diametrically opposite one another and arranged on the joining segments of the cylindrical shell, are provided.

The advantage of this feature is that the oval cover can be closed uniformly because of the two diametrically opposite closures.

In a further embodiment of the invention, at least one connector for delivering a pressure medium into the pressure container is provided in the cover.

The advantage of this feature is that pressure delivery lines of this kind do not interfere with handling when inserting and removing the bag into and from the housing, and then when the cover is set in place and closed, preparation is then also automatically made for delivering the pressure medium.

In a further embodiment of the invention, the inner wall of the housing is equipped with a low-friction lining.

This feature has the considerable advantage, in terms of handling, of further facilitating introduction of the bag into the upright hollow-cylindrical body that is open at the top. The reason is that the bags are usually made from plastic materials, and the material of the pressure container will usually be metal, and thus two materials which because of their differing material structures do not slide particularly well along one another must move past each other. The provision of the low-friction lining, made in particular of a smooth Teflon material or the like, means that the bag slides smoothly into the housing.

In a further embodiment of the invention, the entire pressure container can be mounted on a stand.

As mentioned initially, the simple and lightweight design is an essential advantage of the invention. It is thereby possible to mount even relatively large pressure containers on stands that are common in medical technology, usually so-called rolling stands.

In a further embodiment of the invention, the housing is joined to the cover in lossproof fashion via an apparatus that can be extended and retracted along the stand axis.

The advantage of this feature is that the cover cannot inadvertently be misplaced during handling or, if applicable, during a later cleaning operation; rather these two essential components are joined to one another in lossproof fashion. Thanks to the apparatus that can be retracted and extended along the stand axis, the housing can be displaced relative to the cover or vice versa, for example in order to remove an empty bag and introduce a full bag. This further facilitates handling with simple features.

In a further embodiment of the invention, the apparatus is of telescoping configuration.

The advantage of this feature is to allow the use of slender telescopes extending along the stand axis, which do not require a great deal of installation space and do not constitute bulky components which interfere with handling of the pressure container.

In a particularly preferred embodiment, the cover can be joined immovably to the stand, and the housing is displaceable along the stand axis relative to the cover.

This feature has the considerable advantage, in terms of handling, that the cover, optionally with various connectors, can be mounted in stationary fashion on the stand, and that in order to install or remove a bag, the housing is lowered relative to the cover and then raised up again.

In a further embodiment of the invention, there is provided in the apparatus a load-relieving spring which facilitates the operation of displacing the housing.

This feature has the considerable advantage, in terms of handling, that thanks to the load-relieving spring these raising and lowering operations can be easily performed without exerting effort, i.e. that even physically delicate operators can perform such changing operations, since springs of this kind can exert a constant force over the entire linear stroke.

In a further embodiment of the invention, the spring is a gas spring, a scroll spring, or a spring with a shape-memory alloy.

The advantage of this feature is that the load-relieving lowering or raising operation can be performed easily and safely using such springs, since such springs exert a constant force over the entire linear stroke.

In a further embodiment of the invention, a hooking apparatus for the bag is provided on the underside of the cover.

This feature has the considerable advantage, in terms of handling, that after the housing has been lowered, for example, an empty bag can be unhooked and a new, full bag can be hooked onto the underside; this can be performed in simple and easily handled fashion. The housing is then brought up to the cover from below, and the pressure container is closed using the closures.

In a further highly preferred embodiment of the invention, there is provided in the upper edge of the housing at least one cutout into which the fluid discharge line of the container can be set from above and thereby guided out of the housing.

This feature has the considerable advantage, in terms of handling, that the fluid discharge line of the bag does not need to be threaded through an opening or connected to a separate connector in the housing, which might possible be the source of contamination. This placement operation is easy to perform, especially with the aforementioned raising and lowering of the housing. Once the bag has been hooked onto the underside, the housing is brought up to the cover from below; the operator then merely needs to place the fluid discharge line into the cutout which is open at the top, an operation which not only lies directly within the operator's field of view but also does not require a great deal of attention. For large housings it is also possible to provide several cutouts, so that two or more bags can be introduced and their fluid discharge lines can each be individually led out of the pressure container.

In a further embodiment of the invention, a shaped seal, into which the fluid discharge line can be placed, can be set into the cutout.

The advantage of this feature is that sealing is reliably guaranteed. The shaped seal can either already be provided on the fluid discharge line or can be slid onto it before placement.

In a further embodiment of the invention, a segment of the cover which overlaps the upper edge of the housing also partially covers the shaped seal.

The advantage of this feature is that this point can be sealed in particularly reliable fashion, since the pressure existing in the interior presses the shaped seal in effectively sealing fashion against the overlapping segment from the inside.

In a further embodiment of the invention, the shaped seal overlaps the housing wall internally and externally in the region of the cutout.

The advantage of this feature is that a shaped seal of this kind can easily be inserted from above into the cutout and moreover fits around the cutout over a relatively large surface area, thus ensuring excellent sealing.

In a further embodiment of the invention, the shaped seal is slotted so that the fluid discharge line can be pushed into the shaped seal.

This feature has the considerable advantage, in terms of handling, that mounting of the seal onto the tube, or vice versa, can be performed more simply. Either the seal can be pushed onto the tube using the slot, or the seal is first placed into the cutout and then the fluid discharge line tube is pushed in.

In a further embodiment of the invention, a heater is provided on the housing.

This feature has the considerable advantage that the bags received in the pressure container can be kept warm or heated as necessary.

In a further embodiment of the invention, a basket into which the bag can be placed is mounted on the cover.

The advantage of this feature is that the flexible bag is held in position and supported in the basket, thus making it possible, especially with large bags, to prevent the occurrence of contact over a large area between the bag and the inner wall of the housing. This not only greatly facilitates the placement or introduction of the bag into the interior of the pressure container, but also makes it possible for an erroneously introduced bag that is still completely full to be removed again from the pressure container. Especially in the embodiment in which the windows which close off the viewing openings are mounted from the inside, there would be a risk that the bag might get caught on the windows. When a large bag, for example one with a capacity of 5 liters, or two bags of, for example 1.5 liters capacity, are placed into the pressure container, this operation is greatly facilitated by the basket. When unsupported, very large and heavy bags assume the shape of a very wide droplet, so that contact with the inner wall of the chamber might then occur over a large area. This is now reliably prevented by the basket.

In a further embodiment of the invention, the basket has a bottom which comes to rest at a distance above the closed bottom of the housing.

The fluid discharge line extends out from the bottom of the bag and must be guided through a 180-degree loop from the bottom of the bag to the upper edge of the pressure container. If the bottom of the bag were to come to rest on the bottom of the pressure container housing, the line could be kinked and discharge of the fluid could be blocked. The bag can now be laid on the bottom of the basket, and there is still sufficient room available under the bottom to allow unhindered passage of the tube.

In a further embodiment of the invention, the basket has a guide for the fluid discharge line of the bag.

The considerable advantage of this feature is that because of the guide on the basket, the fluid discharge line can be led in positionally defined fashion to the upper end of the pressure container, so that tangling or jamming cannot occur as the bag is being installed and removed. In addition, the guide makes it easier to lower the bag into the interior of the pressure container. This accurately reproducible guide for the fluid discharge line also ensures that the latter comes to rest at the point at which it is led out of the pressure container, thus ensuring that the line is not inadvertently pinched when the cover is set in place.

In a further embodiment of the invention, the guide has hooks into which the fluid discharge line can be introduced.

The advantage of this feature is that the line can very easily be placed, slid, or threaded into the hooks, and can also be secured by appropriate configuration and alignment of the hooks.

In a further embodiment of the invention, the bottom is made of a rod element bent in serpentine fashion.

The considerable advantage of this feature is that the bottom-mounted outlet or connector fitting of the flexible bag can be laid between the serpentine turns and fixed in position there. This configuration, in combination with the fact that this bottom comes to rest at a distance above the bottom of the housing, ensures that regardless of the bag length or any sagging of the bag, the height position of the lower connector is reproducible and fixed, thus reliably preventing any kinking of the outgoing discharge line.

In a further embodiment of the invention, the heater is configured as a wall of the basket.

The advantage of this feature is that the bag introduced into the basket directly receives maximum possible contact with the heater, thus greatly improving efficiency. The fact that the heater is accommodated in the interior of the pressure container also maximizes efficiency in terms of thermal radiation.

In a further embodiment of the invention, provision is made for the control elements pertinent to the heater to be mounted on the cover.

The advantage of this feature is that the control elements which are connected to the heater are mounted on a component, namely the cover, on which the basket whose wall is configured as the heater is also mounted, thus making possible easy handling and a simple configuration for these components.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be explained and described more detail below with reference to several selected exemplifying embodiments in conjunction with the appended drawings, in which:

FIG. 6 shows a greatly enlarged partial side view, rotated 90 degrees with respect to the representation of FIG. 2, of the housing with the cover in place, the rotary closure being located in its end position;

FIG. 7 shows a section along line VII—VII in FIG. 6;

FIG. 9 shows a side view of the complete pressure container of the second embodiment, mounted on a stand with the housing lowered;

FIG. 10 shows a side view corresponding to FIG. 9, with the pressure container closed;

DETAILED DESCRIPTION OF PREFERRED EMBODIMENTS

Figure 1:
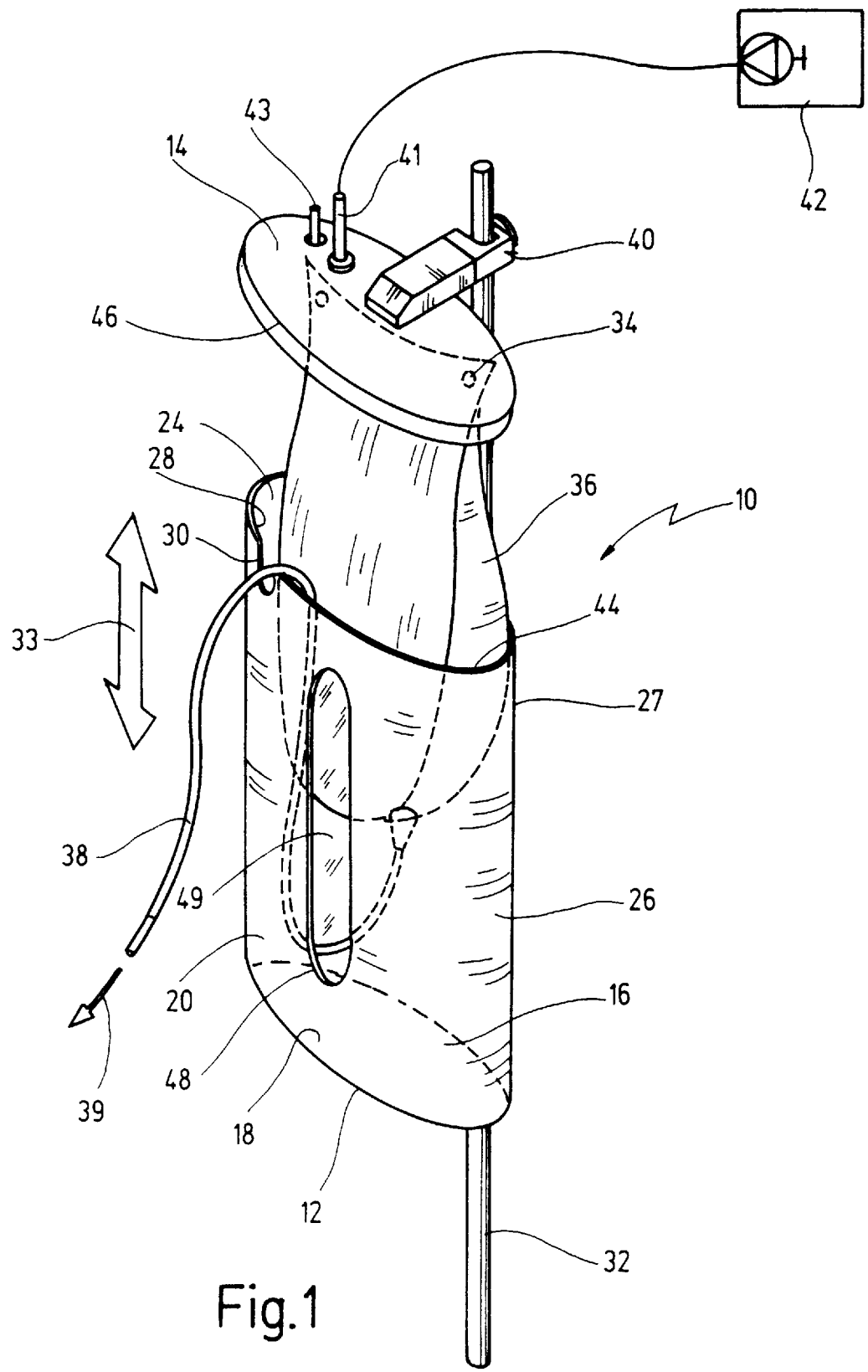
FIG. 1 hows, in highly schematized fashion, a first exemplary embodiment of a pressure container according to the present invention.

FIG. 1 shows a pressure container designated in its entirety with the reference number 10.

Pressure container 10 has a housing 12 and a cover 14 detachable therefrom.

Housing 12 comprises an upright, approximately hollow-cylindrical body 16 which is closed off at the bottom by a bottom 18.

Housing 12 has two opposing sidewalls 20, 22 arranged in mirror-image fashion, which are joined to one another by joining segments 24 and 26.

Sidewalls 20 and 22 have the form of a cylindrical shell segment. A cutout 30, whose purpose will be described later, is provided in an upper edge 28 of housing 12.

Cover 14 is attached removably via a mount 40 to a stand 32. A hooking apparatus 34, into which a bag 36 can be hooked, is provided on the underside of cover 14.

A bag 36 is made of a flexible plastic material and is filled with a medical fluid (not described further here). A fluid discharge line 38, immovably joined to bag 36, leads away from the lower end thereof, specifically in the form of a tube welded onto bag 36.

A connector fitting 41 that can be connected via a line to a pressure source 42 is present on cover 14. A pressure relief valve is also provided on the cover.

It is evident from the perspective representation that hollow-cylindrical body 16, open at the top, has in cross section the shape of a flattened oval, thus resulting at the upper end in an oval opening 44 which roughly corresponds to the cross-sectional contour of bag 36, so that the latter can be received snugly in the chamber delimited by body 16.

A window 48, closed off by a pane 49 applied from the inner side, is provided in sidewall 20.

A heater (not shown here) in the form of a planar heating pad is provided on housing 12, in order either to keep the fluid contained in bag 36 warm (at, for example, 37 or 42 degrees C), or to heat it as necessary.

Pressure container 10 is handled as follows: In order to put in place a bag 36 filled with a fluid, housing 12 is lowered, i.e. displaced downward along stand 32. Bag 36 is then hooked onto the underside of cover 14. Housing 12 is then slid from below over bag 36 hanging on cover 14. The operator grasps fluid discharge line 38 with one hand and ensures that it comes to rest from above in cutout 30. Housing 12 is pushed up until its upper edge 28 comes to rest against the underside of cover 14. For this purpose, an oval-shaped V-seal (not shown here) is placed between housing 12 and cover 14. Cover 14 has a downwardly projecting overlapping segment 46 which is configured so that it also partially covers cutout 30, so that provision can then be made for fluid discharge line 38 to be led outward in sealed fashion, as will be described later in further detail in connection with other exemplifying embodiments. Once housing 12 has been correspondingly displaced, as indicated by double arrow 33, cover 14 is firmly attached to housing 12 via a closure (not shown here).

A gaseous pressure medium, for example compressed air or $CO_2$, can then be introduced via pressure source 42 into the interior, i.e. the pressure chamber, of pressure container 10, thus gradually building up a pressure. This pressure causes bag 36 to be compressed, and causes the fluid contained therein to be discharged from pressure container 10 through fluid discharge line 38, as indicated by an arrow 39. The respective fill level of bag 36 can be observed through window 48. Once bag 36 is empty or the flushing operation is complete, the interior is vented to atmospheric pressure, the closure (not shown) is opened, and housing 12 can be lowered again so that the now-empty bag 36 can be removed and another one inserted.

Because fluid discharge line 38 is passed through cutout 30, fluid discharge line 38 does not need to be threaded through a hole, for example in the bottom, so that fluid discharge line 38 provided by the manufacturer can be connected directly, without interposition of a connecting line or passthrough line, for example to the instrument through which the flushing fluid is to be delivered.

The configuration of the closure and the pressure-tight pass-through for the fluid discharge line out will be explained and described in more detail in conjunction with FIGS. 2 through 10.

The pressure container shown in FIGS. 2 through 10 is designated in its entirety with the reference number 50.

Pressure container 50 again, as described earlier, has a housing 52 and a cover 54.

Figure 2:
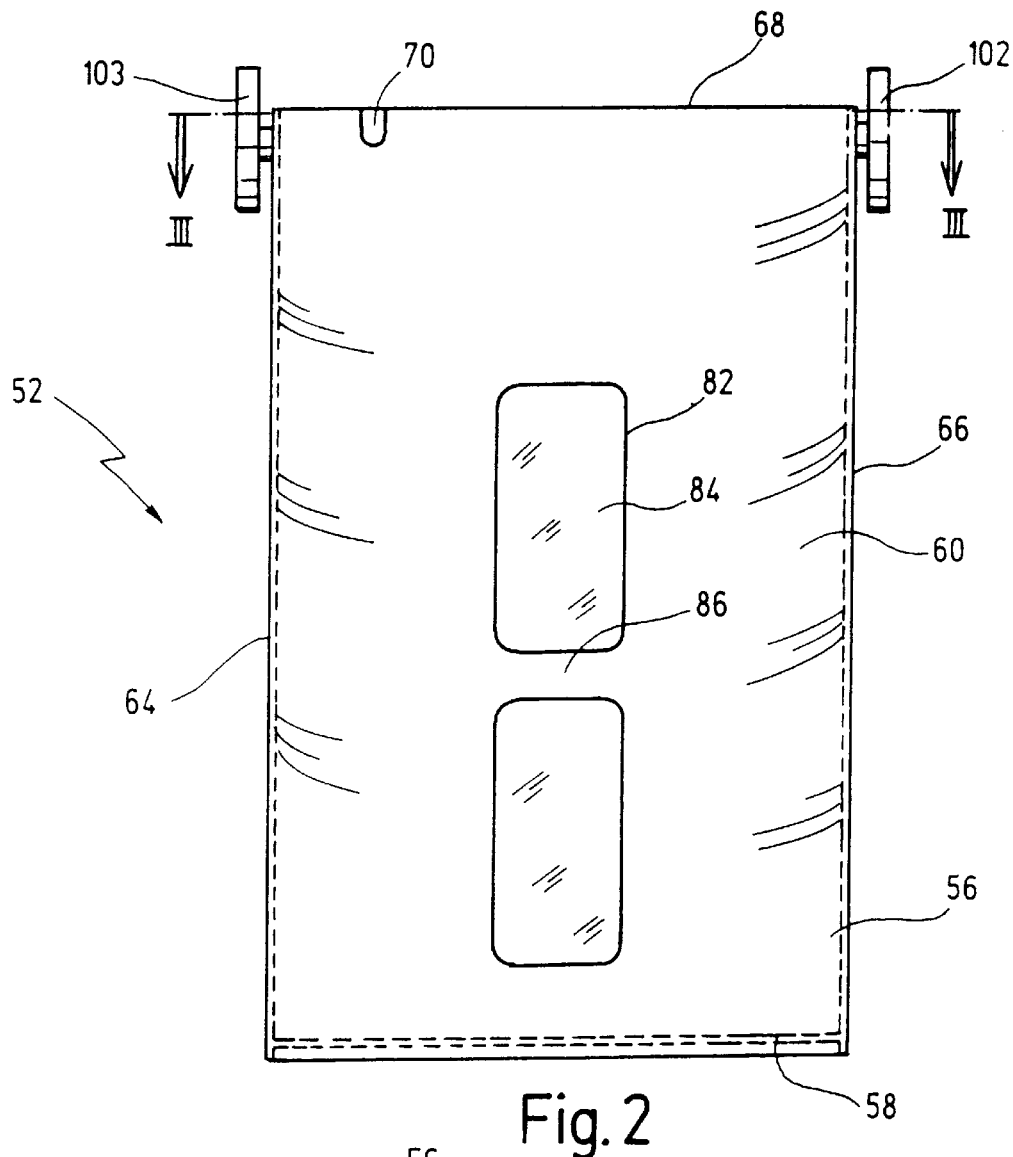
FIG. 2 hows a side view of a housing of a second exemplifying embodiment of a pressure container according to the present invention, without the cover in place.
Figure 3:
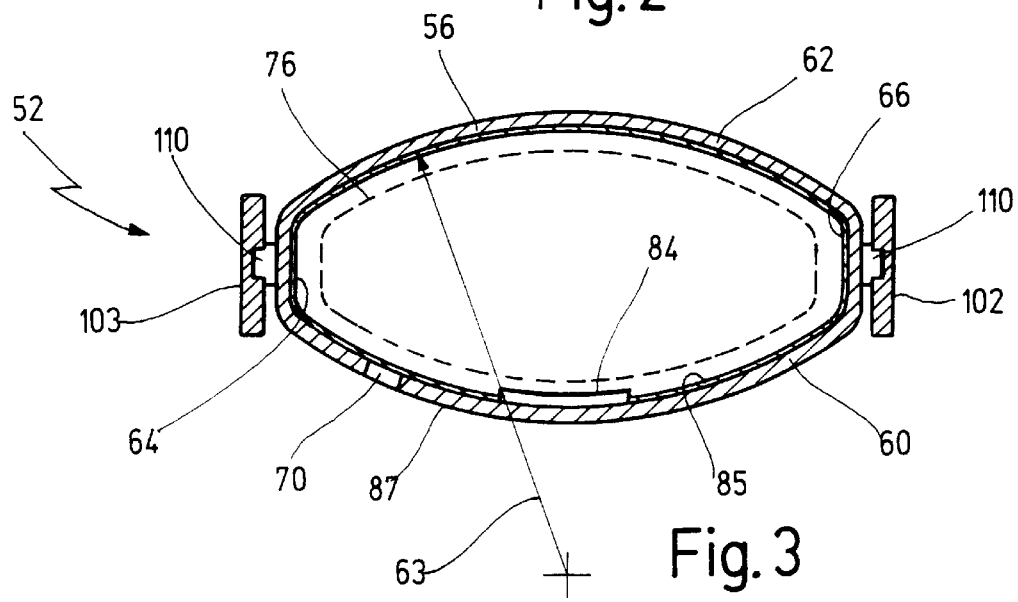
FIG. 3 hows a cross section along line III—III in FIG. 2.

Housing 52 has, as is evident in particular from the representations of FIGS. 2 and 3, an upright hollow-cylindrical body 56, open at the top and closed off at the lower end by a bottom 58.

Body 56 has two outwardly curved sidewalls 60 and 62, located opposite one another in mirror-image fashion, which are joined together by flattened joining segments 64 and 66. In FIG. 3, a radius 63 indicates that sidewall 62 is configured as a segment of a cylindrical shell having a radius 63. The same applies to sidewall 60. Provided in upper edge 68, as described earlier, is a cutout 70 which allows fluid discharge line 78 to pass through. It is evident from FIG. 9 that cover 54 is mounted on a stand 72 via a mount 124.

A hooking apparatus 74, onto which a bag 76 is hooked, is once again provided on the underside of cover 54. A fluid discharge line 78 in the form of a tube leads away from the bottom of bag 76. A medical fluid 80 is received in bag 76, which is made of a transparent plastic material. A pressure valve can be arranged in the connection region of fluid discharge line 78, so that, for example in the position shown in FIG. 9, fluid cannot flow out by gravity, but rather can do so only if a certain applied pressure is exceeded.

Returning to FIG. 2, it is evident therefrom that a window 82, closed off by a transparent pane 84, is provided in sidewall 60.

As is evident from the sectioned representation of FIG. 3, pane 84 is placed against inner wall 85 in the region of window 82, and also has the shape of a cylindrical shell segment. Window 82 is divided into two segments of approximately equal size by a horizontally extending strip 86 of material. Strip 86 not only increases the stability of sidewall 60, but also represents an additional support for pane 84 to prevent bulging.

Inner wall 85 of the overall housing 52 is equipped with a low-friction lining 87, for example a Teflon coating.

Figure 5:
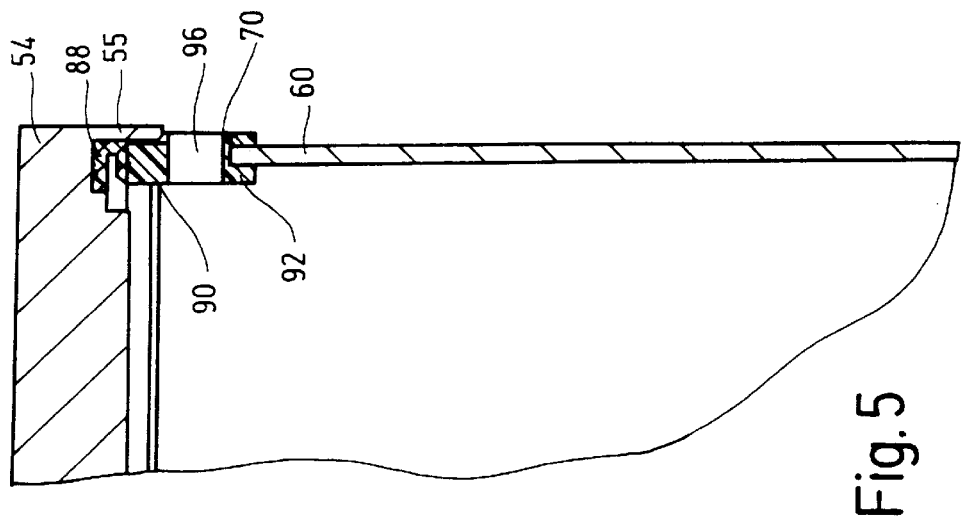
FIG. 5 shows a section along line V—V in FIG. 4.
Figure 4:
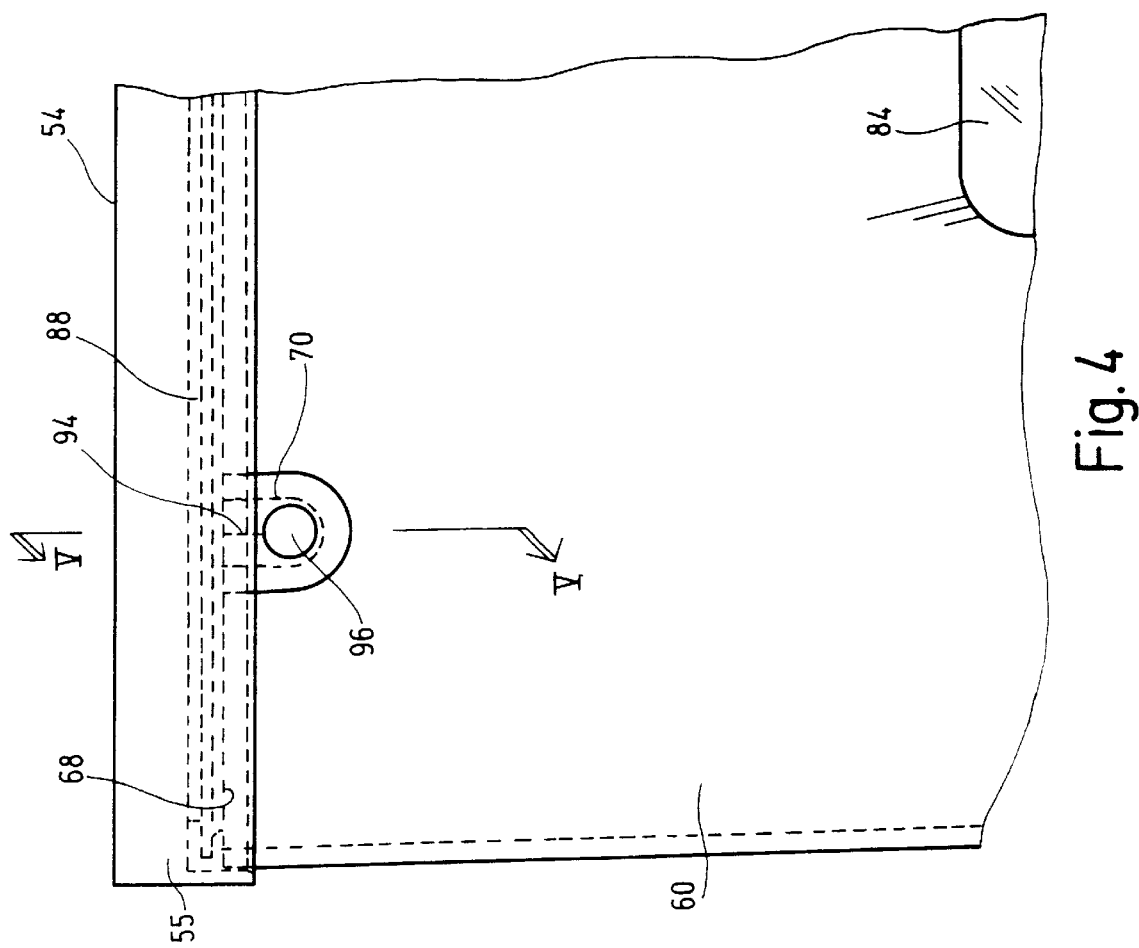
FIG. 4 hows a greatly enlarged partial representation of the container of FIG. 2 in the region of a cutout for leading the fluid discharge line through with the cover in place.

Located on upper edge 68 is a circumferential V-seal 88, as is evident in particular from the enlarged sectioned representations of FIGS. 4 and 5.

V-seal 88 thus also covers cutout 70 in upper edge 68.

A shaped seal 90 is additionally placed into cutout 70, as is also evident from the sectioned representations of FIGS. 4 and 5.

Shaped seal 90 has a substantially U-shaped body which is placed from above into cutout 70. Shaped seal 90 has regions 92 which overlap sidewall 60 on both sides, so that it covers the wall regions delimiting cutout 70 on both the inside and the outside. At the upper end, shaped seal 90 extends up to the underside of V-seal 88. When cover 54 is set in place, its downwardly directed overlapping segment 55 thus overlaps or covers the upper region of shaped seal 90, and extends to a point close to its center opening 96, through which fluid discharge line 78 of bag 76 passes in sealing fashion.

Depending on the configuration, shaped seal 90 can previously be slid by the manufacturer onto fluid discharge line 78; it is also possible to do this in situ. Further simplification is achieved by the fact that shaped seal 90 is equipped in the upper region with a continuous slot 94, so that the tube of fluid discharge line 78 can be pushed in from above. The reason is that in pressurized operation, shaped seal 90, as is evident in particular from the representations of FIGS. 4 and 5, is then covered in the slotted region by the overlapping segment 55 of cover 54, so that the applied pressure provides an additionally sealing effect which is additionally ensured by the spreading of V-seal 88.

Figure 8:
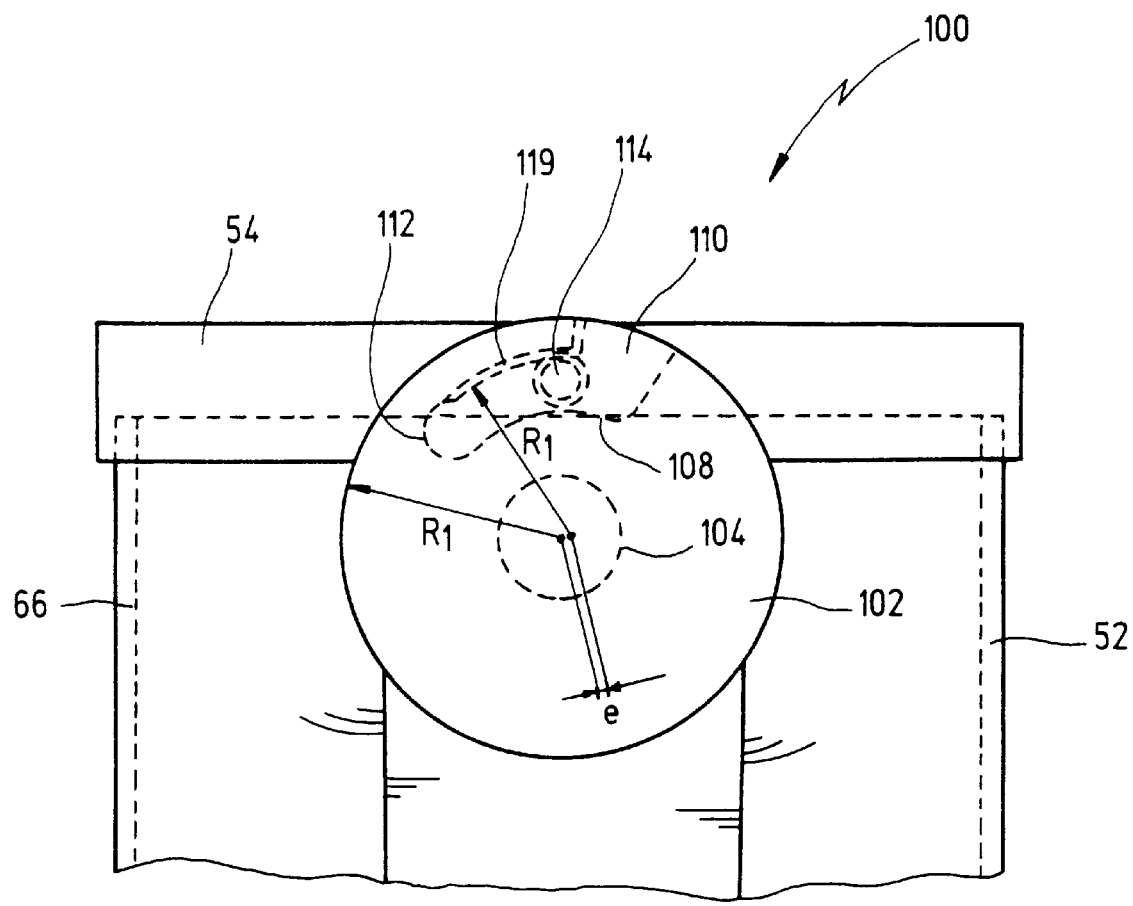
FIG. 8 shows a representation comparable to the representation of FIG. 6, with the closure in a different operating position.

FIGS. 6 through 8 depict in more detail closures 100 for closing pressure container 50.

Each closure 100 has, on diametrically opposite joining segments 64 and 66 of housing 52, turning knobs 102 and 103 mounted rotatably on the exterior via radially projecting pivot pins 104.

A gated guide 106 is cut out on the inner side of each turning knob 102, 103 in the form of a groove 108 cut thereinto.

Groove 108 has a radially terminating opening 110 through which a gate peg 114, projecting radially outward from overlapping segment 55 of cover 54, can enter.

As is evident in particular from FIG. 7, gate peg 114 has an end on which a roller 116 or a needle bearing is rotatably mounted; and a solid shoulder segment 118 is located farther inward.

It is evident from the sectioned representation of FIG. 6 that groove 108, extending approximately in the direction of the circumference of turning knob 102, has a ramp 119 which is configured such that after gate peg 114 has entered groove 108 through opening 110 and turning knob 102 has been rotated, gate peg 114 initially rolls via roller 116 along one flank of groove 108. As is evident from FIG. 7, gate peg 114 is not in contact with its shoulder segment 118 against the flank of groove 108 until turning knob 102 has rotated to the point that gate peg 114 has reached a stop 112. Roller 116 is then no longer resting against a flank of groove 108.

This configuration facilitates both handling and the rotary motion of turning knob 102 when closing closure 100, operations that are facilitated by the rolling motion of roller 116. Only in the end position does shoulder segment 118 rest positively in stop 112; because of the solid configuration of shoulder segment 118, the forces acting on closure 100 in pressurized operation can be easily withstood.

Thus in order to place cover 54 onto housing 52, turning knobs 102 are rotated so that openings 110 of groove 108 face upward, as is evident from FIG. 3. By setting cover 54 in place, its radially projecting gate pegs 114 enter groove 108 through its opening 110. Gate peg 114 is then brought against stop 112 by rotation of turning knob 102.

It is evident from FIG. 8 that although the profile of ramp 119 is circumferential in shape, the necessary closing force is gradually applied as a result of eccentricity e. When shoulder segment 118 has reached stop 112, the latter sits firmly in an undercut or a kind of trough, thus creating a certain self-holding force or preload, so that closure 100 cannot be opened even by inadvertent jostling of turning knobs 102. The operator palpably detects the snapping action into the undercut. This holding force also ensures that, as described above, shaped seal 90 and V-seal 88 are already in sealing contact against one another, thus ensuring that fluid discharge line 78 passes in gas-tight fashion out of pressure container 50. In pressurized operation, the undercut ensures that closure 100 cannot be opened either inadvertently or deliberately, since to do so cover 54 would need to be moved against the closing force, which is not possible manually.

FIGS. 9 and 10 show that cover 54 mounted on stand 72 is joined to housing 52 via an apparatus 120.

Apparatus 120 has a triple telescope 122 in whose interior a load-relieving spring 126 is arranged. Load-relieving spring 126 is configured so that the weight of housing 52 is compensated for, i.e. it can be displaced along stand 72 very easily, and will stay in position at any height.

In the representation of FIG. 9, housing 52 is lowered sufficiently that a bag 76 can be hooked onto hooking apparatus 74 on the underside of cover 54. Housing 52 is then raised, as indicated in FIG. 10 by an arrow 129. It is now important to ensure that fluid discharge line 78 is placed into cutout 70 in the upper edge or into shaped seal 90 received therein. Housing 52 is raised until the radially projecting gate pegs 114 of cover 54 have entered opening 110 of groove 108 of gated guide 106. Turning knobs 102 are then rotated, as indicated in FIG. 10 by an arrow 129 on turning knob 102. Closure 100 is thereby closed, i.e. cover 54 is joined in gas-tight fashion to housing 52; fluid discharge line 78 projects out of pressure container 50 and can then be connected to appropriate equipment.

During operation, the pressure medium can be introduced through connector 128 into the internal pressure chamber of pressure container 50, and fluid 80 is thereby pushed out of bag 76 and carried off through fluid discharge line 78.

Figure 11:
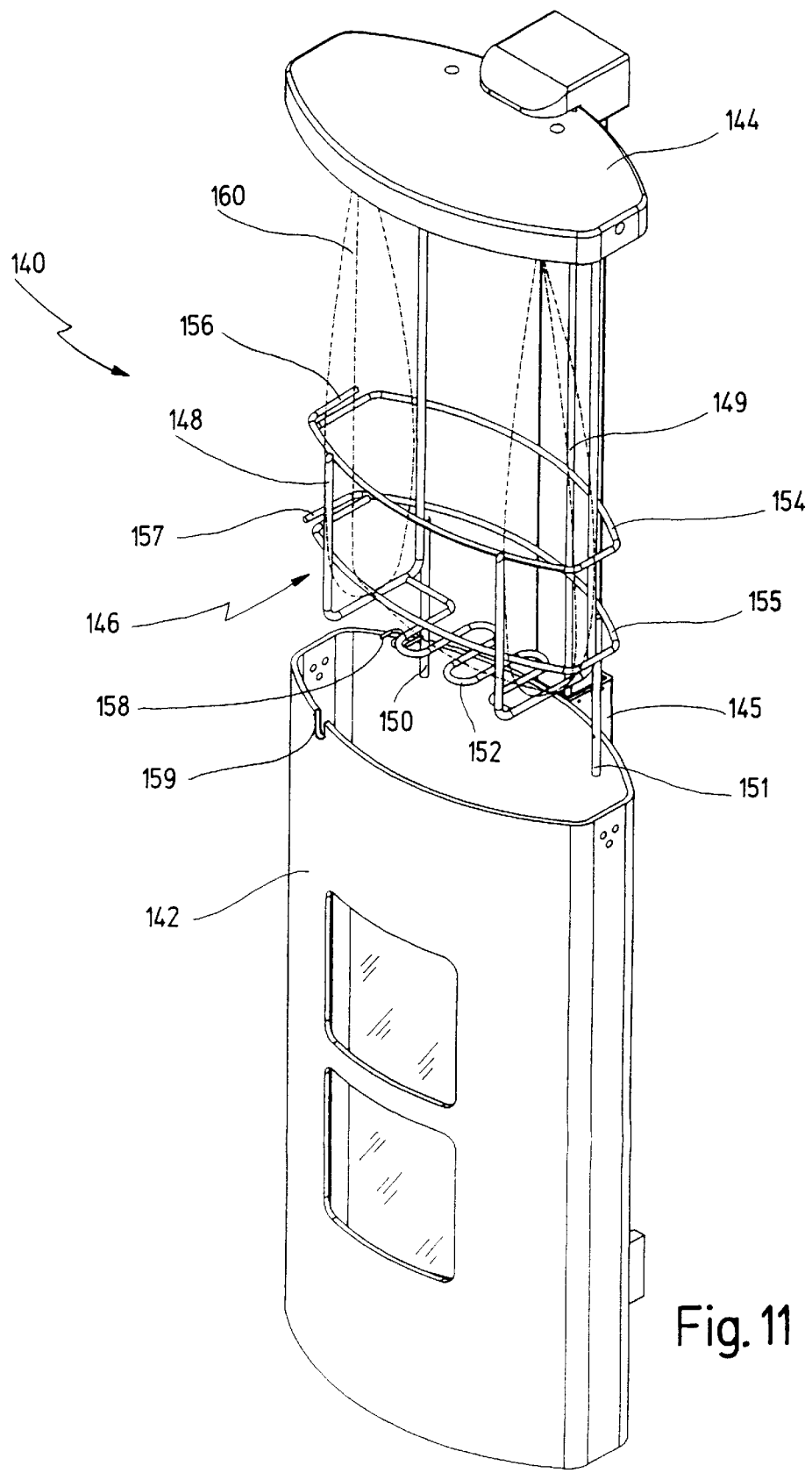
FIG. 11 shows a representation comparable to FIG. 1 of a further exemplifying embodiment with a basket mounted on the cover for receiving the bag.
Figure 12:
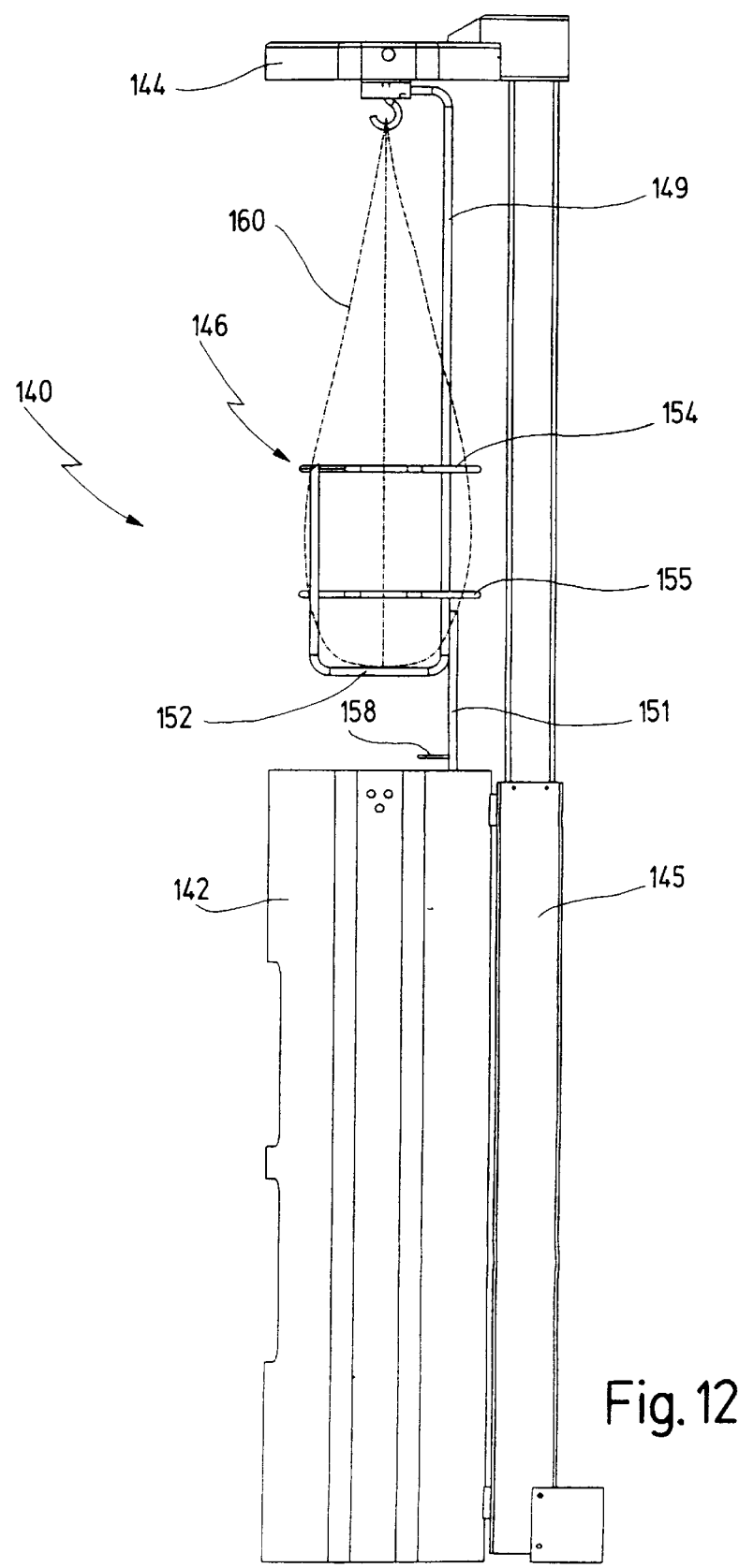
FIG. 12 shows a side view of the representation of FIG. 11.

In the further exemplifying embodiment of a pressure container 140 shown in FIGS. 11 and 12, the latter has a housing 142 which is equipped, in a manner similar to the exemplifying embodiment described in FIGS. 2 through 10, with two windows (not designated here in detail).

A cover 144 can be raised and lowered relative to the housing via an apparatus 155 that is displaceable in telescoping fashion, as described previously in connection with the embodiment of FIGS. 9 and 10. For the sake of clarity, the closures are not shown.

Mounted on the underside of cover 144 is a basket 146 that is provided to receive one or more bags 160.

Bag 146 has two side brackets 148, 149 whose lower end regions are bent into a U-shape.

Projecting respectively from the lower ends of side brackets 158, 159 are rods 150, 151 which serve as spacers or support feet for basket 146 with respect to the closed bottom of housing 142.

The two side brackets 148, 149 are joined to one another by two hoops 154, 155.

The contour of hoops 154, 155 corresponds approximately to the cross-sectional contour of housing 142, and they are dimensioned so that they come to rest at a distance from the inner wall of housing 142.

Hoops 154, 155 each comprise a rod bent into an oval. The outer ends of the bent rods laterally overlap one another, thereby forming hooks 156 and 157 into which the fluid discharge line (not shown here for the sake of clarity), in the form of a loop as shown in FIG. 1, can be laterally inserted.

Bottom 152 of basket 146 is configured as a rod bent into a serpentine or meander shape, thus forming niche-like regions into which a downwardly protruding connector fitting of bag 160 can be placed, as shown, for example, in the case of bag 36 in FIG. 1.

As is evident from FIG. 1, the tube line proceeding from the bottom of the bag must be bent into a 180-degree loop and guided upward. This guidance is effected by hooks 156 and 157 described earlier, and by a further hook 158 that is provided on rod 150.

As is evident from the representation of FIG. 12, bag 160 is held by basket 146 in such a way that contact with the inner wall of housing 142 over a large area cannot occur. The connector fitting (not shown here for the sake of clarity) projecting downward from the bottom of bag 160 can be placed between the serpentine turns of bottom 152. There is enough space available beneath bottom 152 for the emerging tube to be led upward through 180 degrees in the form of a loop. It is then threaded or inserted into hooks 158, 157, 156 and thereby guided in secure and positionally immobilized fashion to cutout 159 at the upper end of housing 142, through which the line is then led out of the housing. Bag 160 received in basket 146 is also suspended in a hook on the underside of cover 144.

If a heater is provided, it can be configured as one wall of the basket, so that a bag placed into the basket is then in contact with the heater over a large area.

What is claimed is:

1. A pressure container for applying a pressure to a flexible bag containing a fluid, said flexible bag provided with a discharge line, via which discharge line said fluid is discharged when pressure is applied to said bag, said container comprising a housing having an opening for inserting said flexible bag into said housing, a cover for closing said opening of said housing, an aperture in said container for passing said discharge line of said flexible bag out of said container, a closure for sealingly joining said cover and said housing, and means for delivering a pressure medium into said container, wherein said housing is configured as an upright hollow-cylindrical body, closed at a bottom and open at a top thereof, a cross-section of said housing has a flattened oval shape and corresponds roughly to a cross-sectional contour of said flexible bag, and wherein two opposing large area upright sidewalls of said housing, each have, in mirror-image fashion, a shape of a segment of a cylindrical shell whose lateral ends are joined by joining segments.

2. The pressure container of claim 1, wherein said cover is configured as a cover covering an oval upper opening of said upright hollow-cylindrical body and overlapping an upper edge area of said body.

3. The pressure container of claim 1, wherein there is provided in at least one of said sidewalls a viewing window, a pane of said window has also a shape of a cylindrical shell element, and wherein said pane is placed against said viewing window from an inner side of the housing.

4. The pressure container of claim 3, wherein at least one strip of a material of said sidewall is left behind in said viewing window, said strip is crossing said viewing window.

5. The pressure container of claim 1, wherein said closure is provided with at least one turning knob arranged on an outer side of said housing, on an inner side of said turning knob a gated guide is cut out, into which gate a gate peg projecting radially from said cover can be introduced, and wherein by rotation of said turning knob, said gate sealingly prevents removal of said cover from the housing.

6. The pressure container of claim 5, wherein said gate peg has a cylindrical shoulder segment, projecting radially from said cover, adjoining which is an end equipped with a bearing, said gated guide being configured such that in a first rotational section said bearing runs over a ramp, and only in an end position an end section of said gated guide provided with a stop come to rest against a shoulder segment of said gate peg.

7. The pressure container of claim 6, wherein said gated guide is undercut in an area of said stop.

8. The pressure container of claim 1, wherein a circumferential V-seal is provided between said cover and said upper edge of said body.

9. The pressure container of claim 1, wherein two closure arrangements, diametrically opposite one to another and arranged on said joining segments of said cylindrical shell walls, are provided.

10. The pressure container of claim 1, wherein said means for delivering a pressure medium into said container comprises at least one connector provided in said cover.

11. The pressure container of claim 1, wherein an inner wall of said housing is equipped with a low-friction lining.

12. The pressure container of claim 1, wherein said container can be mounted on a stand.

13. The pressure container of claim 12, wherein said housing is joined to said cover in lossproof fashion via an apparatus that can be extended and retracted along an axis of said stand.

14. The pressure container of claim 13, wherein said apparatus is of telescoping configuration.

15. The pressure container of claim 14, wherein said cover can be joined immovably to said stand, and wherein said housing is displaceable along said stand axis relative to said cover.

16. The pressure container of claim 15, wherein a load-relieving spring is provided in said apparatus, which spring facilitating an operation of displacing of said housing.

17. The pressure container of claim 1, wherein a hooking apparatus for hooking in said bag is provided at an underside of said cover.

18. The pressure container of claim 1, wherein said aperture for passing said discharge line is designed as at least one cutout provided in an upper edge of said housing.

19. The pressure container of claim 18, wherein a shaped seal can be set into said at least one cutout, into which shaped seal said fluid discharge line can be placed.

20. The pressure container of claim 19, wherein a section of said cover overlapping an upper edge of said housing also partially covers said shaped seal.

21. The pressure container of claim 20, wherein said seal overlaps a wall of said housing internally and externally in an area of said cutout.

22. The pressure container of claim 21, wherein said shaped seal is provided with a slot, via which slot said fluid discharge line can be pushed into said shaped seal.

23. The pressure container of claim 1, wherein a heater is provided at said housing.

24. The pressure container of claim 1, wherein a basket, into which said bag can be placed, is mounted on said cover.

25. The pressure container of claim 24, wherein said basket is provided with a bottom which comes to rest at a distance above said closed bottom of said housing.

26. The pressure container of claim 25, wherein said basket is provided with a guide for guiding said fluid discharge line of said bag.

27. The pressure container of claim 26, wherein said guide for said fluid discharge line has hooks into which said fluid discharge line can be introduced.

28. The pressure container of claim 27, wherein said bottom of said basket is made of rod elements bent in serpentine fashion.

29. The pressure container of claim 28, wherein a wall of said basket is configured as a heater.

30. The pressure container of claim 29, wherein control elements, pertinent to said heater, are mounted on said cover.

* * * * *

UNITED STATES PATENT AND TRADEMARK OFFICE
CERTIFICATE OF CORRECTION

PATENT NO. : 6,096,007
DATED : August 1, 2000
INVENTOR(S) : Harald Haan, et. al.

It is certified that error appears in the above-indentified patent and that said Letters Patent is hereby corrected as shown below:

Title page, item [30], should read --

Foreign Application Priority Data

August 1, 1997 [DE] Germany 197 33 278

Signed and Sealed this

Tenth Day of April, 2001

Attest:

NICHOLAS P. GODICI

*Attesting Officer*   *Acting Director of the United States Patent and Trademark Office*